US011564559B2

(12) United States Patent
Ide

(10) Patent No.: US 11,564,559 B2
(45) Date of Patent: Jan. 31, 2023

(54) INSERTION PORTION OF ENDOSCOPE AND ENDOSCOPE TO WHICH THE INSERTION PORTION IS APPLIED

(71) Applicant: OLYMPUS CORPORATION, Tokyo (JP)

(72) Inventor: Yuka Ide, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 369 days.

(21) Appl. No.: 16/799,954

(22) Filed: Feb. 25, 2020

(65) Prior Publication Data
US 2020/0187765 A1 Jun. 18, 2020

Related U.S. Application Data

(63) Continuation of application No. PCT/JP2018/026067, filed on Jul. 10, 2018.

(30) Foreign Application Priority Data

Sep. 5, 2017 (JP) .............................. JP2017-170442

(51) Int. Cl.
*A61B 1/005* (2006.01)
*A61B 1/06* (2006.01)
(Continued)

(52) U.S. Cl.
CPC ............ *A61B 1/0057* (2013.01); *A61B 1/005* (2013.01); *A61B 1/0661* (2013.01); *A61B 1/07* (2013.01);
(Continued)

(58) Field of Classification Search
CPC ..... A61B 1/0057; A61B 1/0661; A61B 1/005; A61B 1/07; A61B 1/0055; G02B 23/2469; G02B 23/26
See application file for complete search history.

(56) References Cited

U.S. PATENT DOCUMENTS 6,013,024 A 1/2000 Mitsuda et al.
2006/0252993 A1 11/2006 Freed et al.

FOREIGN PATENT DOCUMENTS

JP S62-246358 A 10/1987
JP H03-86143 A 4/1991
(Continued)

OTHER PUBLICATIONS

International Search Report dated Oct. 9, 2018 issued in PCT/JP2018/026067.

*Primary Examiner* — Aaron B Fairchild
*Assistant Examiner* — Christen A. Sharpless
(74) *Attorney, Agent, or Firm* — Scully, Scott, Murphy & Presser, P.C.

(57) ABSTRACT

An insertion portion of an endoscope includes a multi-lumen tube including a treatment instrument insertion channel, a first wire insertion hole that is provided parallel to the treatment instrument insertion channel, and a second wire insertion hole; one towing wire including a first portion that is inserted into the first wire insertion hole, a second portion that is inserted into the second wire insertion hole, and a third portion that is drawn out between the first wire insertion hole and the second wire insertion hole, wherein a proximal end portion of the first portion and a proximal end portion of the second portion are connected to a bending operation member; and a third wire insertion hole into which the third portion is inserted and in which the third portion abuts on a part of an inner peripheral surface.

20 Claims, 7 Drawing Sheets

(51) Int. Cl.
 *A61B 1/07* (2006.01)
 *G02B 23/24* (2006.01)
 *G02B 23/26* (2006.01)
(52) U.S. Cl.
 CPC ......... *G02B 23/2469* (2013.01); *G02B 23/26* (2013.01)

(56) References Cited

FOREIGN PATENT DOCUMENTS

| | | | |
|---|---|---|---|
| JP | H0386145 A | * | 4/1991 |
| JP | H08-94941 A | | 4/1996 |
| JP | H0894941 A | * | 4/1996 |
| JP | H10-258022 A | | 9/1998 |
| JP | 2001-231742 A | | 8/2001 |
| JP | 2009-112536 A | | 5/2009 |
| JP | 2009-530051 A | | 8/2009 |
| JP | 2010017401 A | * | 1/2010 |
| WO | WO 2005/094665 A2 | | 10/2005 |

* cited by examiner

INSERTION PORTION OF ENDOSCOPE AND ENDOSCOPE TO WHICH THE INSERTION PORTION IS APPLIED

CROSS REFERENCE TO RELATED APPLICATION

This application is a continuation application of PCT/JP2018/026067 filed on Jul. 10, 2018 and claims benefit of Japanese Application No. 2017-170442 filed in Japan on Sep. 5, 2017, the entire contents of which are incorporated herein by this reference.

BACKGROUND OF THE INVENTION

1. Field of the Invention

The invention relates to an insertion portion of an endoscope configured using a multi-lumen tube, and an endoscope to which the insertion portion is applied.

2. Description of the Related Art

Conventionally, endoscopes including an elongated tube-shaped insertion portion have been widely used, for example, in a medical field, an industrial field, or the like.

In the endoscopes, a medical endoscope used in the medical field is configured so that an insertion portion can be inserted, for example, into a body cavity of a living body to observe an organ, etc., or various treatments of the organ, etc. can be performed using a treatment instrument inserted into a treatment instrument insertion channel included in the endoscope, if necessary.

Further, an industrial endoscope used in the industrial field is configured so that an insertion portion can be inserted into, for example, a jet engine, an apparatus such as factory piping, or an inside of mechanical equipment, etc. and a state of damage or corrosion, etc. in the apparatus or mechanical equipment can be observed and inspected.

In an insertion portion of a conventional endoscope of this sort, an insertion portion having soft flexibility and including a bending portion formed in a freely bendable manner by an operation at hand is put to practical use. By including such a configuration, an insertability into a subject of the insertion portion of the endoscope is improved.

Further, in the medical endoscope, particularly, in the endoscope for renal pelvis/urinary, bronchial tubes, or the like, a small diameter of the insertion portion is always desired. Therefore, in the above endoscopes, it is desirable to avoid a large diameter of the insertion portion as much as possible by complicating a bending mechanism.

To solve the above problem, in the insertion portion of the conventional endoscope, various insertion portions in which a flexible tubular member such as a multi-lumen tube is used as a bending member are proposed, for example, in Japanese Patent Application Laid-Open Publication No. 08-94941 or the like.

In the insertion portion of the endoscope disclosed by Japanese Patent Application Laid-Open Publication No. 08-94941 described above or the like, the multi-lumen tube is used as the bending member. Further, a wire insertion lumen in the multi-lumen tube is cut from an outer peripheral side so as to be cut substantially vertically. Further, a cut in a shape in which a width is gradually widened toward an outer side is arrayed in plurality apart intervals in an axial direction in substantially the same direction.

In the case, the bending operation wire is configured so as to be made to be inserted into one lumen of a pair of wire insertion lumens from the operation portion side and project to a distal end front face of the multi-lumen tube. Then, the bending operation wire is configured so as to be folded along the distal end front face, made to be inserted into the other wire insertion lumen and arranged on the operation portion side.

By using such a configuration, a diameter of the insertion portion is made small at a low cost by using the multi-lumen tube and a desired bending shape is obtained by a light operating force.

SUMMARY OF THE INVENTION

An insertion portion of an endoscope according to one aspect of the present invention includes a multi-lumen tube including a treatment instrument insertion channel, a first wire insertion hole that is provided parallel to the treatment instrument insertion channel, and a second wire insertion hole that is provided parallel to the treatment instrument insertion channel, one towing wire including a first portion that is inserted into the first wire insertion hole, a second portion that is inserted into the second wire insertion hole, and a third portion that is provided between the first portion and the second portion and is drawn out between the first wire insertion hole and the second wire insertion hole, wherein a proximal end portion of the first portion and a proximal end portion of the second portion are connected to a bending operation member, and a third wire insertion hole into which the third portion is inserted and in which the third portion abuts on a part of an inner peripheral surface.

An endoscope according to one aspect of the present invention includes the insertion portion of an endoscope.

DETAILED DESCRIPTION OF THE PREFERRED EMBODIMENTS

Figure 1:
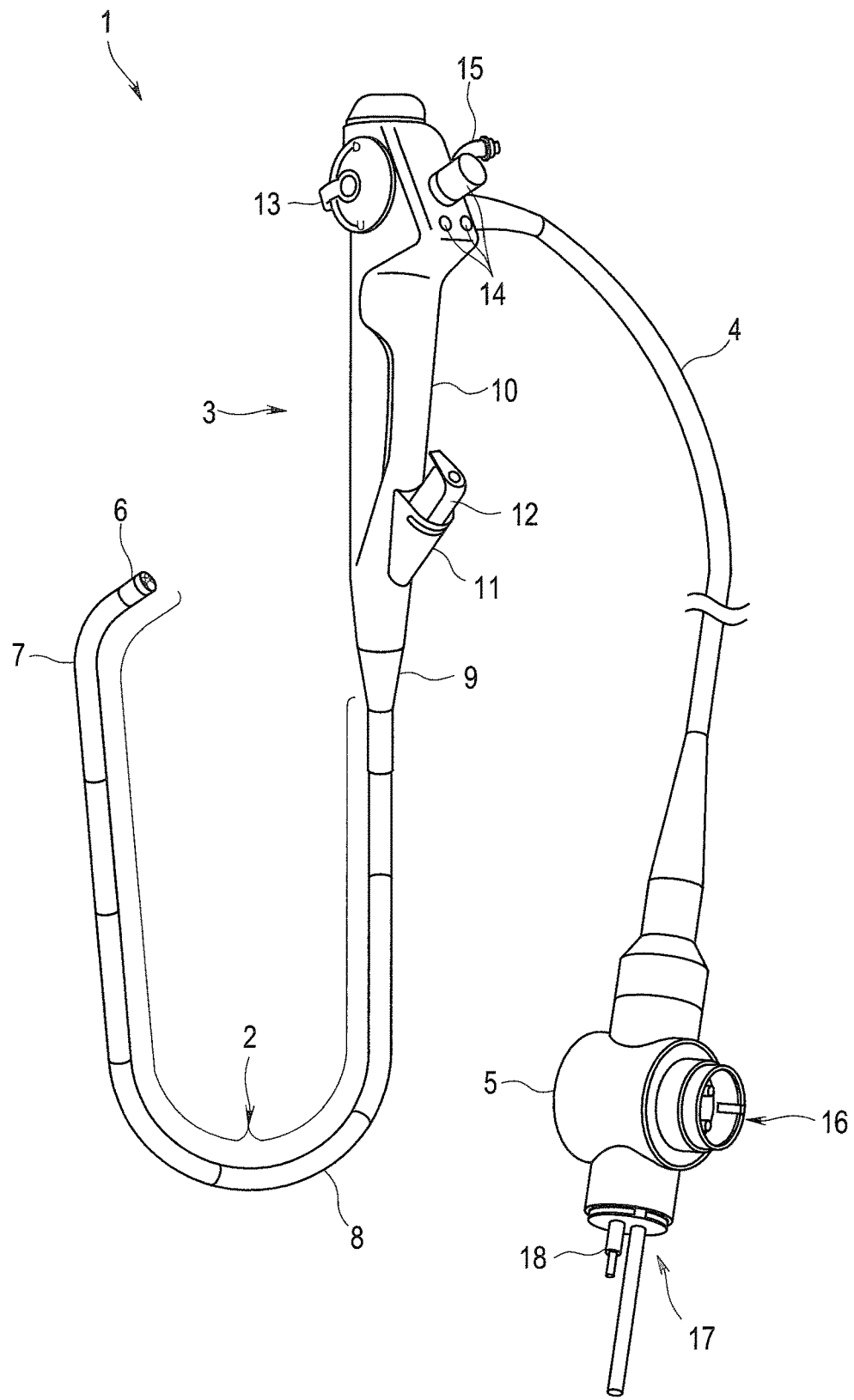
FIG. 1 is a perspective view showing an outline configuration of an endoscope to which an insertion portion of an endoscope of the present invention is applied.

Hereinafter, the present invention will be described with reference to shown embodiments. Each drawing used for the following description is schematically shown, and in order to show each component in a size recognizable in the drawing, a dimensional relationship, scale, etc. of each member may be different for each component. Therefore, the present invention is not limited only to shown forms with respect to the number of components, shapes of the components, a ratio of the sizes of the components, a relative positional relationship between the components, and the like, which are described in these drawings.

First Embodiment

First, before describing a detailed configuration of an insertion portion of an endoscope according to a first embodiment of the present invention, an outline configuration of the whole endoscope to which the insertion portion is applied will be described below with reference to FIG. 1. FIG. 1 is a perspective view showing an outline configuration of the endoscope to which the insertion portion of the endoscope of the present invention is applied.

An endoscope 1 is mainly configured by an insertion portion 2, an operation portion 3, a universal cord 4, an endoscope connector 5, and the like.

The insertion portion 2 is a tubular member that is formed in an elongated tubular shape and is inserted into a subject. The insertion portion 2 is formed by connecting a distal end portion 6, a bending portion 7, and a flexible tube portion 8 in the order from a distal end side and has flexibility as a whole.

In the above-described portions, the distal end portion 6 includes an image pickup unit that is an image pickup apparatus including an image pickup device, etc. internally and an illumination unit that emits illumination light in a forward direction, and the like (either is not shown).

Note that, as a form of the endoscope to which the present invention can be applied, the present embodiment is not limited to one example (an electronic endoscope including the image pickup unit, etc.) described above. A form other than the above form, for example, a form in which an image guide fiber is arranged in the insertion portion 2 without including the image pickup unit, a so-called fiber scope, etc. may be used.

The bending portion 7 is a mechanical unit that is configured so as to receive a rotation operation of a bending lever 13 that is the bending operation member for performing a bending operation among operation members (to be described later) provided on the operation portion 3 and so as to be actively bent in two directions of up and down.

Note that, as a form of the bending portion in the endoscope to which the present invention can be applied, the present embodiment is not limited to one example (a type capable of being bent in two directions of up and down) described above. Further, the present embodiment may be a type, etc. capable of being bent in four directions including left and right directions (that is, a whole peripheral direction around an axis of the insertion portion 2 by each operation in up, down, left, and right directions) in addition to up and down directions.

The flexible tube portion 8 is a tubular member that is formed with flexibility so as to be freely flexible passively. Inserted through the inside of the flexible tube portion 8 are, in addition to a treatment instrument insertion channel (to be described later), various electric signal lines extending from the image pickup unit housed in the distal end portion 6 to the inside of the universal cord 4 through the inside of the operation portion 3, a light guide (not shown) that guides light emitted from a light source apparatus (not shown) that is an outside instrument to an illumination window (not shown) provided on a distal end surface of the distal end portion 6, and the like.

Note that, with regard to a light source, a form in which a light emitter (e.g., a light emitting diode (LED) or the like) is provided on the inside of the operation portion may be used. In the case of the configuration, the above-described light guide (not shown) is used for guiding light emitted from an LED in the operation portion 3 to the illumination window of the distal end portion 6. Further, as an alternative form, a form may be employed in which a light emitter of an LED, etc. is provided on the inside of the distal end portion 6, for example, on a portion near to a distal end of the illumination window. In the case of the configuration, light emitted from the LED directly passes through the illumination window and illuminates a forward direction of the distal end portion 6. Accordingly, in the configuration, it is unnecessary to use the light guide (not shown) in the flexible tube portion 8. On the other hand, a power supply line, etc. for making the LED provided on the distal end portion 6 to emit light is configured to be inserted into the flexible tube portion 8.

The operation portion 3 is a configuration unit that is provided on a proximal end portion of the insertion portion 2 and includes a plurality of operation members, etc. The operation portion 3 is configured by a bend preventing portion 9, a grasping portion 10, the plurality of operation members (13, 14, and the like), a treatment instrument insertion portion 11, a suction valve 15, and the like.

The bend preventing portion 9 is a protection member that is provided in a part connecting a distal end part of the operation portion 3 and a proximal end part of the flexible tube portion 8 and by covering the proximal end part of the flexible tube portion 8, prevents the flexible tube portion 8 from rapidly breaking unnecessarily at the time of using the endoscope 1.

The grasping portion 10 is a chassis portion that houses various constituent members inside. The grasping portion 10 is provided on the bend preventing portion 9. Further, the grasping portion 10 is a portion in which a user grasps the endoscope 1 by a hand at the time of using the endoscope 1.

The plurality of operation members are members that are provided on an outer surface of the grasping portion 10 and operate various functions of the endoscope 1. As the plurality of operation members, an operation member for performing an air/water feeding operation or a suction operation, an operation member 14, etc. for performing operations corresponding to the image pickup unit and the illumination unit, respectively, and the like may be used in addition to the bending lever 13 for performing a bending operation of the bending portion 7, for example.

The treatment instrument insertion portion 11 is a configuration portion that includes a treatment instrument insertion port (not shown) for inserting various treatment instruments (not shown) and includes a treatment instrument insertion path that communicates with the treatment instrument insertion channel in the operation portion 3.

Note that a forceps plug 12 that is a cover member that opens/closes the treatment instrument insertion port and is configured to be detachable (convertible) from the treatment instrument insertion portion 11 is arranged in the treatment instrument insertion portion 11.

Further, the suction valve 15 is a coupling portion that couples suction tube paths between the suction valve 15 and a suction apparatus (not shown).

The universal cord 4 is a hollow tubular member that has flexibility and is extended from the operation portion 3. The universal cord 4 is a composite cable in which various signal lines that are inserted into the inside of the insertion portion 2 from the distal end portion 6 of the insertion portion 2 and are extended through the inside of the operation portion 3, the light guide from the light source apparatus (not shown) that is an outer instrument, an air/water feeding tube, etc. from the air/water feeding apparatus (not shown) that is the outer instrument are inserted into the inside.

The endoscope connector 5 is a connecting member that is arranged on a distal end of the universal cord 4 and secures a connection between the endoscope connector 5 and the outer instrument. The endoscope connector 5 includes, in a side surface portion, an electric connector portion 16 that connects a signal cable for connecting the endoscope connector 5 and a video processor (not shown) that is the outer instrument.

Further, the endoscope connector 5 includes a light guide bundle that connects the endoscope connector 5 and the light source apparatus (not shown) that is an outer apparatus, a light source connector portion 17 that connects an electric cable (now shown) in which the various signal lines are bundled, the air/water feeding plug 18 that connects an air/water feeding tube (not shown) from the air/water feeding apparatus (not shown) that is the outer instrument, and the like.

Subsequently, a detailed configuration of the insertion portion 2 of the endoscope 1 according to the present embodiment will be described below with reference to FIGS. 2 to 6.

Figure 2:
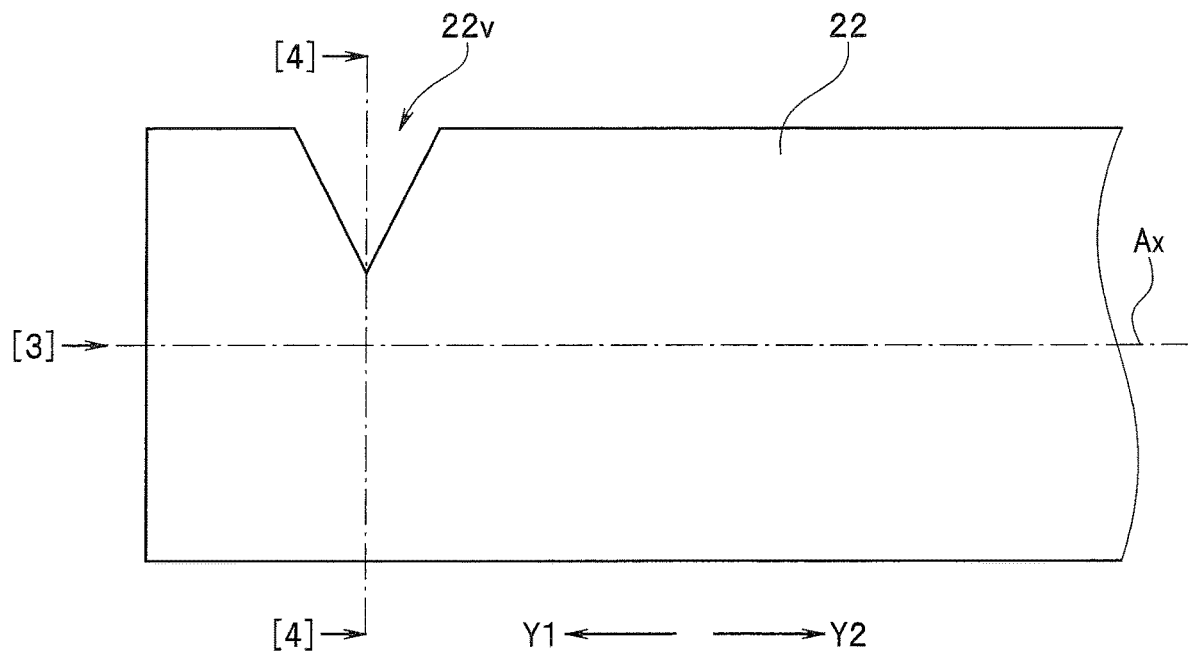
FIG. 2 is a side view enlarging and showing the vicinity of a distal end portion of a multi-lumen tube that is applied to an insertion portion of an endoscope according to a first embodiment of the present invention.

FIG. 2 is a side view enlarging and showing the vicinity of a distal end portion of a multi-lumen tube that is applied to the insertion portion of the endoscope according to the present embodiment. Note that a direction of an arrow Y1 shown in FIG. 2 is supposed to be the distal end side (a direction toward the distal end portion) and a direction of an arrow Y2 shown in the same drawing is supposed to be a proximal end side (a direction toward the operation portion).

Figure 3:
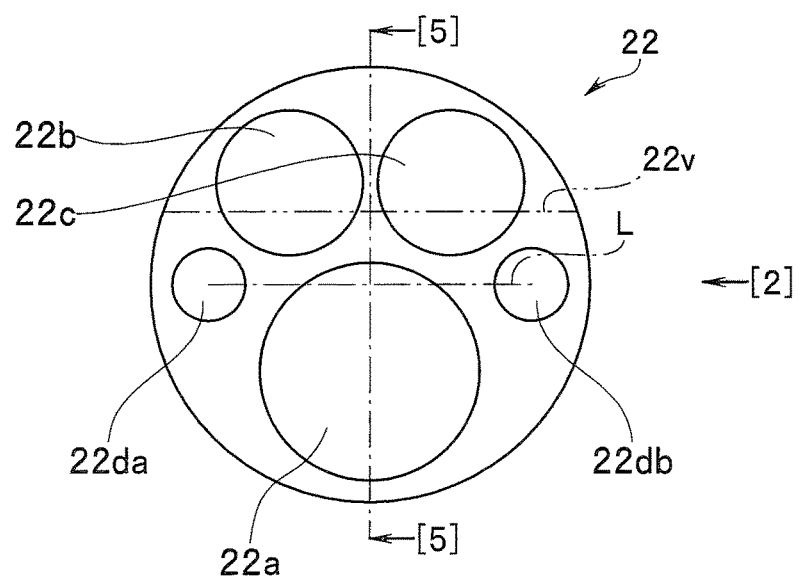
FIG. 3 is a front view of the multi-lumen tube viewed in a direction of an arrow [3] shown in FIG. 2.
Figure 4:
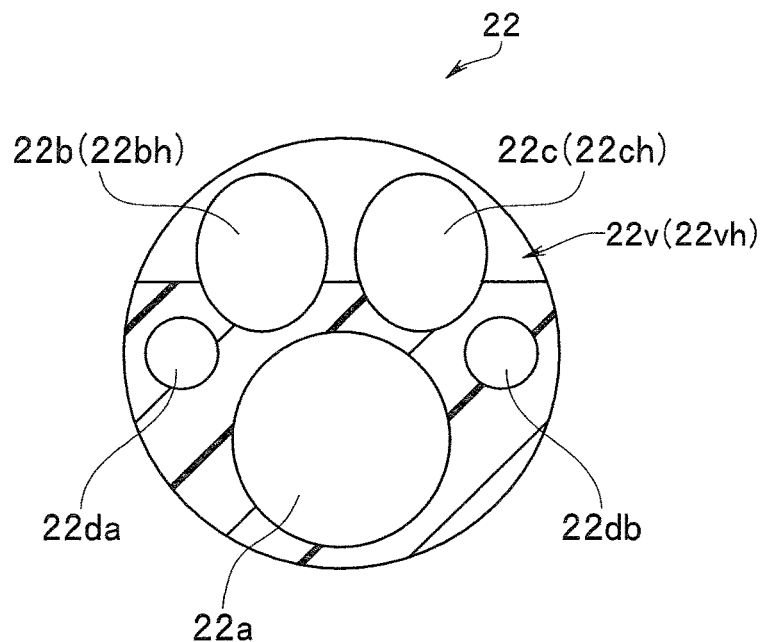
FIG. 4 is a cross-sectional view cut along a line [4]-[4] shown in FIG. 2.
Figure 5:
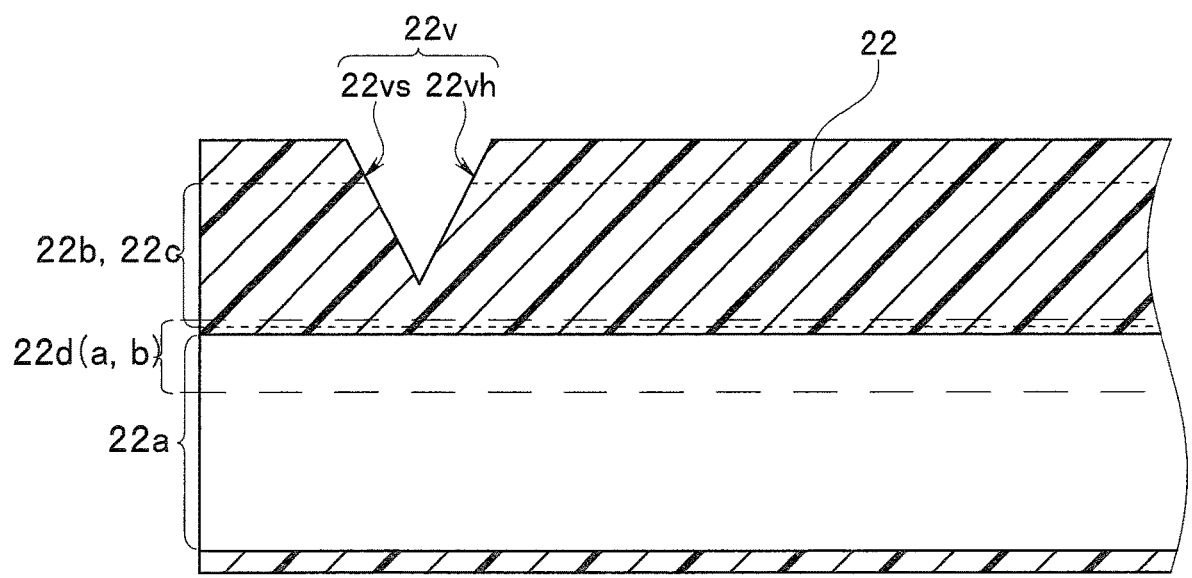
FIG. 5 is a cross-sectional view cut along a line [5]-[5] shown in FIG. 3.

FIG. 3 is a front view of the multi-lumen tube viewed in a direction of an arrow [3] shown in FIG. 2. FIG. 4 is a cross-sectional view cut along a line [4]-[4] shown in FIG. 2. In other words, FIG. 4 is a drawing showing a cross section orthogonal to a long axis of the multi-lumen tube. FIG. 5 is a cross-sectional view cut along a line [5]-[5] shown in FIG. 3. In other words, FIG. 5 is a drawing showing a longitudinal cross section in a direction along the long axis of the multi-lumen tube.

Figure 6:
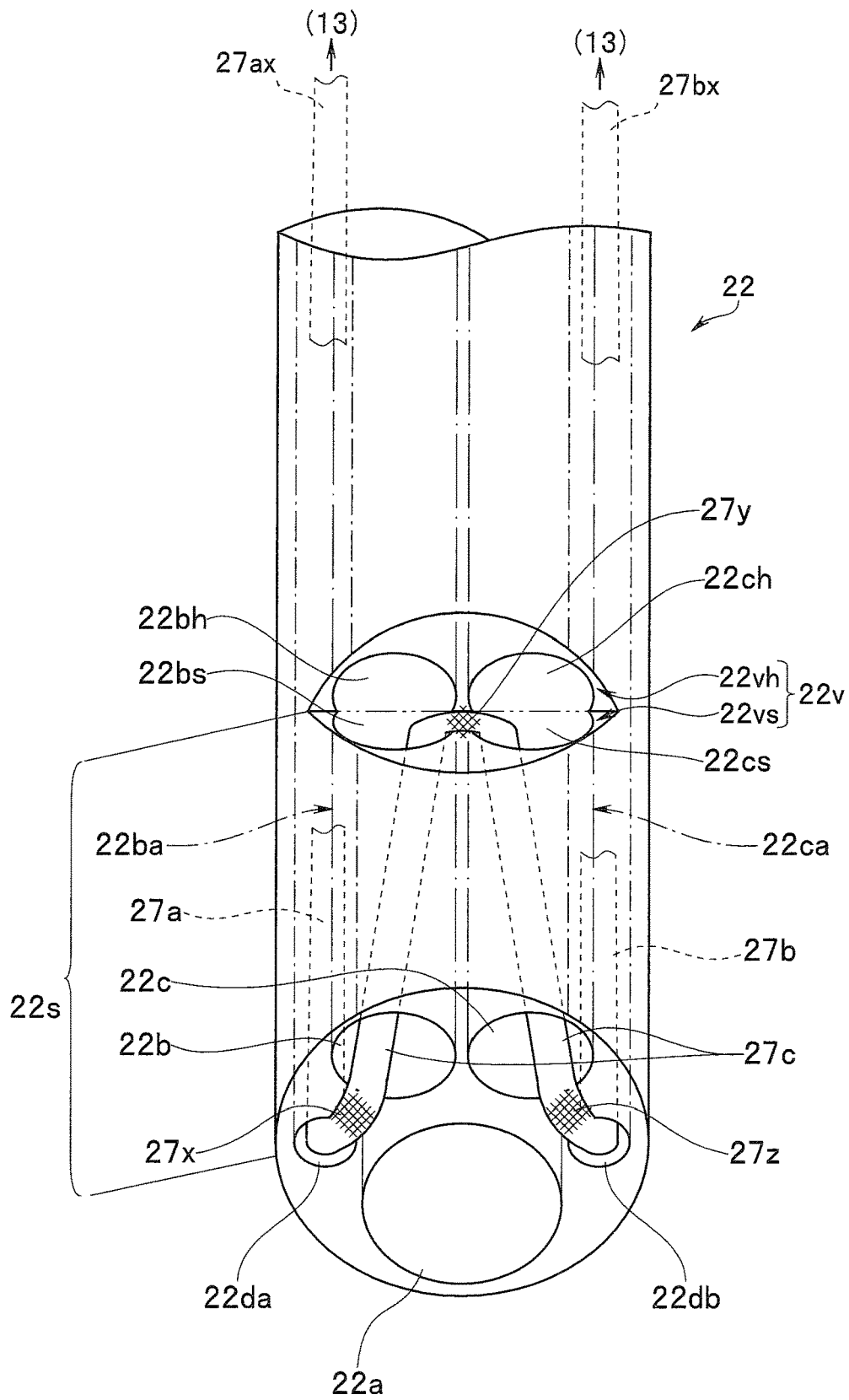
FIG. 6 is a main-part enlarged perspective view enlarging and showing the vicinity of the distal end portion of the multi-lumen tube in a state in which a bending operation wire is assembled into the multi-lumen tube shown in FIG. 2.

FIG. 6 is a main-part enlarged perspective view enlarging and showing the vicinity of the distal end portion of the multi-lumen tube in a state in which a bending operation wire is assembled into the multi-lumen tube shown in FIG. 2.

Note that, in FIGS. 2 to 6, in order to avoid complication in drawings and securely show a configuration of the gist of the present invention, constituent members that are not related to the present invention are not shown where appropriate. Specifically, for example, configurations of a distal end rigid member, an exterior resin layer (shell member) covering outer surfaces of the distal end rigid member and the bending portion, and the like, are not shown. Further, only the multi-lumen tube configuring the insertion portion and the bending operation wire that is inserted and arranged in the multi-lumen tube are shown.

In the insertion portion 2 of the endoscope 1 according to the present embodiment, as described above, the distal end portion 6, the bending portion 7, and the flexible tube portion 8 are provided and formed in the order from the distal end side (see FIG. 1). In FIGS. 2 to 6, the distal end portion 6 is not shown; further, the bending portion 7 is provided on a proximal end of the distal end portion 6 and the flexible tube portion 8 is provided on a proximal end of the bending portion 7.

Here, as a member that configures the bending portion 7 and the flexible tube portion 8, a multi-lumen tube 22 is applied to the insertion portion 2 of the endoscope 1 according to the present embodiment.

The multi-lumen tube 22 is a tubular member in which a plurality of lumens (hole; tubular path) communicating with a direction of a long axis (insertion axis) Ax (see FIG. 2) of the insertion portion 2 are formed. The multi-lumen tube 22 includes at least a treatment instrument insertion channel 22*a*, a first wire insertion hole 22*da* and a second wire insertion hole 22*db* provided parallel to the treatment instrument insertion channel 22*a*.

More specifically, as shown in FIG. 3, the multi-lumen tube 22 in the insertion portion 2 of the endoscope 1 according to the present embodiment includes, for example, the treatment instrument insertion channel 22*a* into which a treatment instrument, etc. are inserted, a light wire material insertion hole 22*b* in which a light guide fiber (LG), etc. are inserted and arranged, a signal line material insertion hole 22*c* in which an electric signal line such as an image pickup signal cable or an image guide fiber (IG), etc. are inserted and arranged, and the first wire insertion hole 22*da* and the second wire insertion hole 22*db* into which bending operation wires 27 (not shown in FIGS. 2 to 5; refer to FIG. 6 to be described later) respectively are inserted.

Here, the first wire insertion hole 22*da* and the second wire insertion hole 22*db* in the multi-lumen tube 22 are provided parallel the treatment instrument insertion channel 22*a* in a direction along an axis Ax. Further, the first wire insertion hole 22*da* and the second wire insertion hole 22*db* are inserted from the proximal end to a distal end of the multi-lumen tube 22 and respective corresponding openings are formed in a proximal end surface and a distal end surface, respectively. Thereby, a first portion 27*a* (see FIG. 6) of a bending operation wire 27 to be described later is inserted and arranged in the first wire insertion hole 22*da*. Further, a second portion 27*b* (see FIG. 6) of the bending operation wire 27 to be described later is inserted and arranged in the second wire insertion hole 22*db*.

Further, as shown in FIG. 3, the first wire insertion hole 22*da* and the second wire insertion hole 22*db* are arranged in a surface orthogonal to the axis Ax. Specifically, the first wire insertion hole 22*da* and the second wire insertion hole 22*db* respectively are arranged in a portion close to an outer peripheral edge so as to face each other across the treatment instrument insertion channel 22*a*.

In the case, in a surface including a line orthogonal to the axis Ax, the first wire insertion hole 22*da* and the second wire insertion hole 22*db* are arranged so that a line L (see FIG. 3) connecting a central point of the first wire insertion hole 22*da* and a central point of the second wire insertion hole 22*db* passes through at least a part of the treatment instrument insertion channel 22*a*.

In other words, the line L connecting the central point of the first wire insertion hole 22*da* and the central point of the second wire insertion hole 22*db* is a line that penetrates the outside and the inside of the treatment instrument insertion channel 22*a*.

Note that respective internal diameters of the first wire insertion hole 22*da* and the second wire insertion hole 22*db* are formed to have a diameter slightly larger than a diameter of the bending operation wire 27 (see FIG. 6) that is inserted into the first wire insertion hole 22*da* and the second wire insertion hole 22*db* respectively.

The multi-lumen tube 22 may be formed of, for example, flexible materials such as expanded PTFE (ePTFE) in which PTFE (polytetrafluoroethylene) that is one of fluoroethylene resins is subjected to drawing processing.

Further, in the multi-lumen tube 22 in the insertion portion 2 according to the present embodiment, a predetermined region in the vicinity of the distal end portion is set to a region corresponding to the bending portion 7. Further, a region that is provided in the bending portion 7 and is extended up to the operation portion 3 (see FIG. 1) is set to a region corresponding to the flexible tube portion 8.

Further, in the multi-lumen tube 22 according to the present embodiment, a cut portion 22*v* is formed in a predetermined portion (for example, a portion close to the proximal end by approximately 1 to 2 centimeters in a long axis direction from the distal end surface) in the vicinity of the distal end portion.

The cut portion 22*v* is cut so as to be orthogonal to an axis direction toward the inside in a radical direction from the outer peripheral side of the multi-lumen tube 22 and is a cut in a shape that becomes gradually increased in width toward the outside. Thereby, the cut portion 22*v* includes two slope portions 22*vs* and 22*vh*. Here, the slope portion 22*vs* is supposed to indicate a slope near to the distal end of the multi-lumen tube 22. Further, the slope portion 22*vh* is supposed to indicate a slope near to a proximal end of the multi-lumen tube 22.

Note that the cut portion 22*v* is formed so as to cut the light wire material insertion hole 22*b* and the signal line material insertion hole 22*c*, respectively, in the multi-lumen tube 22 substantially vertically. Accordingly, thereby, a part of the light wire material insertion hole 22*b* and a part of the signal line material insertion hole 22*c* respectively are exposed to the cut portion 22*v*. Further, a plurality of openings (22*bs*, 22*bh*, 22*cs*, and 22*ch*) are formed in the two slope portions 22*vs* and 22*vh* of the cut portion 22*v*.

Here, among the plurality of openings, one opening 22*bs* of the light wire material insertion hole 22*b* and one opening 22*cs* of the signal line material insertion hole 22*c* are formed in one slope portion 22*vs* of the cut portion 22*v*. Further, among the plurality of openings, the other opening 22*bh* of the light wire material insertion hole 22*b* and the other opening 22*ch* of the signal line material insertion hole 22*c* are formed in the other slope portion 22*vh* of the cut portion 22*v*.

Note that, in the multi-lumen tube 22, a predetermined region on the distal end side from a portion in which the cut portion 22*v* is formed up to a front face of the multi-lumen tube 22 is supposed to be referred to a distal end portion 22*s* (see FIG. 6).

Further, a portion that is a part of the light wire material insertion hole 22*b* and the signal line material insertion hole 22*c* and is provided in a region of the distal end portion 22*s* is supposed to be referred to third wire insertion holes 22*ba* and 22*ca*. A third portion 27*c* (see FIG. 6) of the bending operation wire 27 to be described later is inserted and arranged in the third wire insertion holes 22*ba* and 22*ca*.

As shown in FIG. 6, the bending operation wire 27 is inserted and arranged in the insertion portion 2 including the multi-lumen tube 22 configured as described above.

The bending operation wire 27 that is applied to the endoscope 1 according to the present embodiment is the one towing wire.

As shown in FIG. 6, the bending operation wire 27 includes the first portion 27*a* that is inserted into the first wire insertion hole 22*da*, the second portion 27*b* that is inserted into the second wire insertion hole 22*db*, and the third portion 27*c* that is provided between the first portion 27*a* and the second portion 27*b* and is drawn out between the first wire insertion hole 22*da* and the second wire insertion hole 22*db*. Further, in the bending operation wire 27, a proximal end portion 27*ax* of the first portion 27*a* and a proximal end portion 27*bx* of the second portion 27*b* are connected to the bending lever 13 that is the bending operation member.

Note that, here, the third portion 27*c* of the bending operation wire 27 is inserted into the third wire insertion holes 22*ba* and 22*ca*. At this time, a part of the third portion 27*c* is arranged so as to abut on a part of an inner peripheral surface of the multi-lumen tube 22 (described later in detail).

Here, a procedure when one bending operation wire 27 is assembled into a predetermined portion of the multi-lumen tube 22 will be described briefly.

First, one end portion of the one bending operation wire 27 is made to be inserted from an opening (not shown) on the proximal end side (operation portion 3 side) of the insertion portion 2, that is, an opening on the proximal end side (not shown) of the first wire insertion hole 22*da* of the multi-lumen tube 22 and inserted into the distal end side. Then, one end portion of the bending operation wire 27 projects in a forward direction from the front face opening of the first wire insertion hole 22*da* among front face openings of the plurality of lumens of the multi-lumen tube 22. Here, a portion that is inserted into the first wire insertion hole 22*da* is the first portion 27*a* in the bending operation wire 27.

Subsequently, one end portion of the bending operation wire 27 in a projecting state in the forward direction from the front face opening of the first wire insertion hole 22*da* is inserted into the front face opening of the light wire material insertion hole 22*b* among the front face openings of the plurality of lumens of the multi-lumen tube 22. In other words, the bending operation wire 27 projects in the forward direction from the front face opening of the first wire insertion hole 22*da*. Then, the bending operation wire 27 is folded (a cross-hatching portion represented by a reference numeral 27*x* shown in FIG. 6; see a first folded portion) at the front face of the multi-lumen tube 22 and is inserted into the front face opening of the light wire material insertion hole 22*b*. Further, one end portion of the bending operation wire 27 is inserted into the light wire material insertion hole 22*b* in a region of the distal end portion 22*s* and projects to the proximal end side from an opening on the proximal end side (the one opening 22*bs* of the slope portion 22*vs* of the cut portion 22*v*) of the light wire material insertion hole 22*b*.

Subsequently, one end portion of the bending operation wire 27 in a projecting state to the proximal end side from the one opening 22*bs* of the slope portion 22*vs* is inserted into the opening on the proximal end side (one opening 22*cs* of the slope portion 22vs of the cut portion 22v) of the signal line material insertion hole 22c. In other words, the bending operation wire 27 projects to the proximal end side from the one opening 22bs of the slope portion 22vs. Then, the bending operation wire 27 is folded (a cross-hatching portion represented by a reference numeral 27y shown in FIG. 6; see a second folded portion) by the cut portion 22v and is inserted into one opening 22cs of the same slope portion 22vs. Then, one end portion of the bending operation wire 27 is inserted into a region of the distal end portion 22s in the signal line material insertion hole 22c and projects in the forward direction from the front face opening of the signal line material insertion hole 22c among the front face openings of the plurality of lumens of the multi-lumen tube 22.

Subsequently, one end portion of the bending operation wire 27 in a projecting state in the forward direction from the front face opening of the signal line material insertion hole 22c is inserted into the front face opening in the second wire insertion hole 22db among the front face openings in the plurality of lumens of the multi-lumen tube 22. In other words, the bending operation wire 27 projects in the forward direction from the front face opening in the signal line material insertion hole 22c. Then, the bending operation wire 27 is folded (a cross-hatching portion represented by a reference numeral 27z shown in FIG. 6; see a third folded portion) at the front face of the multi-lumen tube 22 and is inserted into the front face opening of the second wire insertion hole 22db. Further, one end portion of the bending operation wire 27 is made to be inserted into the second wire insertion hole 22db and project to the proximal end side from the opening (not shown) on the proximal end side (the operation portion 3 side) of the insertion portion 2, that is, the opening on the proximal end side (not shown) of the second wire insertion hole 22db of the multi-lumen tube 22. Here, a portion that is inserted into the second wire insertion hole 22db is the second portion 27b of the bending operation wire 27.

Further, the proximal end portion 27ax of the first portion 27a and the proximal end portion 27bx of the second portion 27b in the bending operation wire 27 are finally connected to the bending lever 13 (not shown).

By using such a configuration, when a predetermined bending operation is performed by using the bending lever 13 that is provided on the operation portion 3, for example, the first portion 27a of the bending operation wire 27 is towed by an operation in one direction. Thereby, a region corresponding to the bending portion 7 in the vicinity of a distal end part of the insertion portion 2 is bent in one predetermined direction. In addition, by an operation in the other direction of the bending lever 13, for example, the second portion 27b of the bending operation wire 27 is towed. Thereby, a region corresponding to the bending portion 7 in the vicinity of the distal end part of the insertion portion 2 is bent in the other predetermined direction.

Note that, at this time, that is, in a case in which a towing force amount when a towing force is applied to the bending operation wire 27 is not large, a part of the third portion 27c of the bending operation wire 27 abuts on a part of the multi-lumen tube 22. Thereby, a frictional force is generated and therefore, in the bending operation wire 27, an engagement force is generated in an abutment portion (that is, the first, second, and third folded portions 27x, 27y, and 27z). The process permits a bending action of the bending portion 7 to be obtained.

On the other hand, when a towing force is applied to the bending operation wire 27, in a case in which a large towing force amount is required, an engagement force due to a frictional force in the first, second, and third folded portions 27x, 27y, and 27z runs low, the bending operation wire 27 is slid, and a necessary bending action cannot be obtained in some cases. In consideration of such a case, the abutment portion (the first, second, and third folded portions 27x, 27y, and 27z) between the bending operation wire 27 and the multi-lumen tube 22 may be configured so as to be adhered and fixed, for example, by using an adhesive agent, etc. (see a cross-hatching portion shown in FIG. 6). In the case, for example, at least one portion of the folded portions (the first, second, and third folded portions 27x, 27y, and 27z) of three portions only has to be adhered and fixed. Of course, all the three portions may be adhered and fixed. Note that, in a case in which only one portion is adhered and fixed, a form for adhering and fixing the second folded portion 27y is a most preferable form.

By including such a configuration, the bending operation wire 27 is towed and operated to thereby surely secure a bending operation of the bending portion 7.

As described above, according to the first embodiment, the insertion portion 2 of the endoscope 1 to which the multi-lumen tube 22 is applied includes the bending operation wire 27 that is the one towing wire. In the case, the multi-lumen tube 22 includes the treatment instrument insertion channel 22a, the first wire insertion hole 22da that is provided parallel to the treatment instrument insertion channel 22a, the second wire insertion hole 22db that is provided parallel to the treatment instrument insertion channel 22a, and the third wire insertion holes 22ba and 22ca that are formed on the distal end portion 22s.

Further, the one bending operation wire 27 (towing wire) includes the first portion 27a that is inserted into the first wire insertion hole 22da, the second portion 27b that is inserted into the second wire insertion hole 22db, and the third portion 27c that is provided between the first portion 27a and the second portion 27b and is drawn out between the first wire insertion hole 22da and the second wire insertion hole 22db. Further, the proximal end portion 27ax of the first portion 27a and the proximal end portion 27bx of the second portion 27b are connected to the bending lever 13 that is the bending operation member. Further, the third portion 27c is inserted into the third wire insertion holes 22ba and 22ca and the third portion 27c abuts on one portion (one portion on the inner peripheral surface; the second folded portion 27y) inside the multi-lumen tube 22.

In other words, one portion (the third portion 27c) of the bending operation wire 27 is inserted and arranged in the third wire insertion holes 22ba and 22ca in a region of the distal end portion 22s that is one portion on the distal end side of the multi-lumen tube 22.

In other words, the third wire insertion holes 22ba and 22ca are formed such that two holes (that is, respective front face openings of the light wire material insertion hole 22b and the signal line material insertion hole 22c) of the front face openings of the plurality of lumens (hole; tubular path) of the multi-lumen tube 22 communicate with the proximal end side (that is, opening on the cut portion 22v side; the openings 22bs and 22cs) of the distal end portion 22s of the same multi-lumen tube 22.

Specifically, the cut portion 22v that exposes a part of the light wire material insertion hole 22b and the signal line material insertion hole 22c respectively is provided in a predetermined portion in the vicinity of the distal end portion of the multi-lumen tube 22. Thereby, the third wire insertion holes 22ba and 22ca are formed in a region of the distal end portion 22s of the multi-lumen tube 22.

Further, in the region of the distal end portion 22s of the multi-lumen tube 22, the first portion 27a of the bending operation wire 27 is made to be inserted into the first wire insertion hole 22da, project in the forward direction from the front face opening of the first wire insertion hole 22da, and folded at the first folded portion 27x. Further, the first portion 27a of the bending operation wire 27 is made to be inserted into the third wire insertion hole 22ba, project to the proximal end side from the opening on the proximal end side (22bs) of the third wire insertion hole 22ba, and folded at the second folded portion 27y. Further, the first portion 27a of the bending operation wire 27 is made to be inserted into the third wire insertion hole 22ca, project in the forward direction from the front face opening of the third wire insertion hole 22ca, folded at the third folded portion 27z, and inserted into the second wire insertion hole 22db. Then, both of the proximal end portions 27ax and 27bx of the bending operation wire 27 are connected to the bending lever 13.

By using such a configuration, in the insertion portion 2 of the endoscope 1 according to the present embodiment, by using the one bending operation wire 27, the bending operation wire 27 is arranged so as to perform a plurality of folds in the region of the distal end portion 22s of the multi-lumen tube 22. Accordingly, components for engaging the bending operation wire 27 can be omitted and therefore an increase in a scale of the insertion portion 2 in a direction of the long axis Ax can be suppressed.

In addition, regardless of a layout of the plurality of lumens of the multi-lumen tube 22, a smaller diameter can be maintained and such a configuration makes a contribution to reduction in a manufacturing cost.

Specifically, the line L (see FIG. 6) connecting respective central points of two insertion holes (the first wire insertion hole 22da and the second wire insertion hole 22db) into which the bending operation wire 27 is made to be inserted passes through at least a part of the treatment instrument insertion channel 22a. However, in the multi-lumen tube 22 in a layout arranged as described above, the one bending operation wire 27 does not cover the treatment instrument insertion channel 22a, the bending operation wire 27 can be arranged, and in addition, a certain bending operation can be secured.

Second Embodiment

Next, an insertion portion of an endoscope according to a second embodiment of the present invention will be described later with reference to FIGS. 7 to 10.

Figure 7:
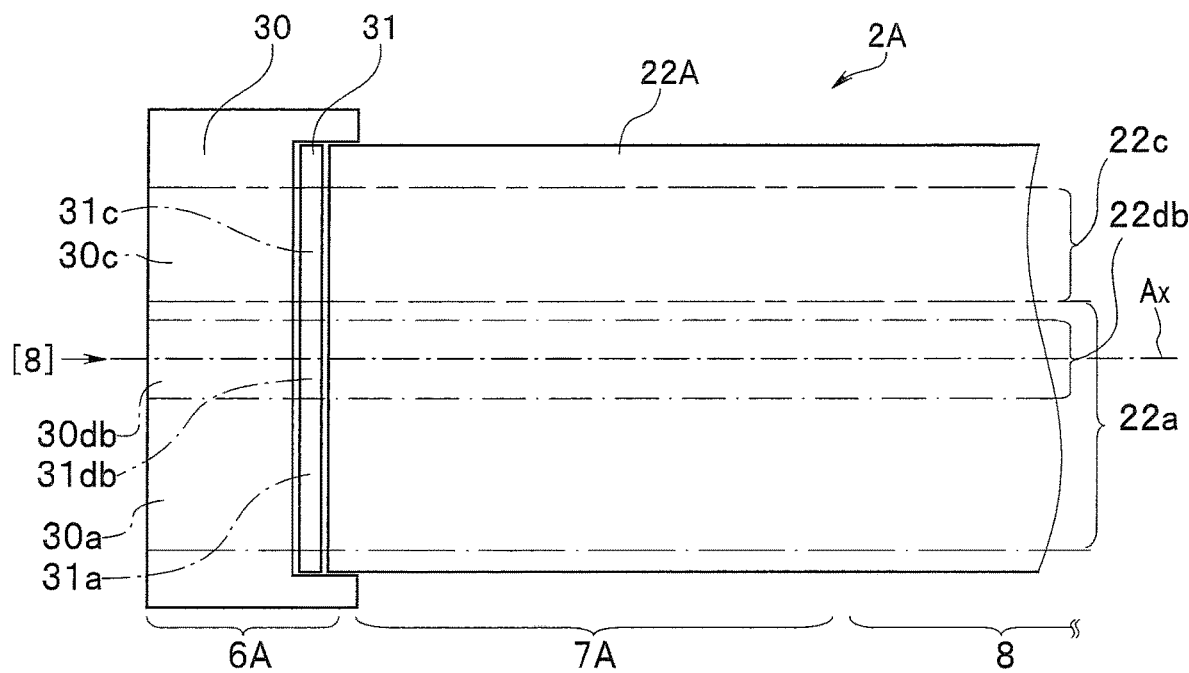
FIG. 7 is a side view enlarging and showing the vicinity of a distal end portion of an insertion portion of an endoscope according to a second embodiment of the present invention.
Figure 8:
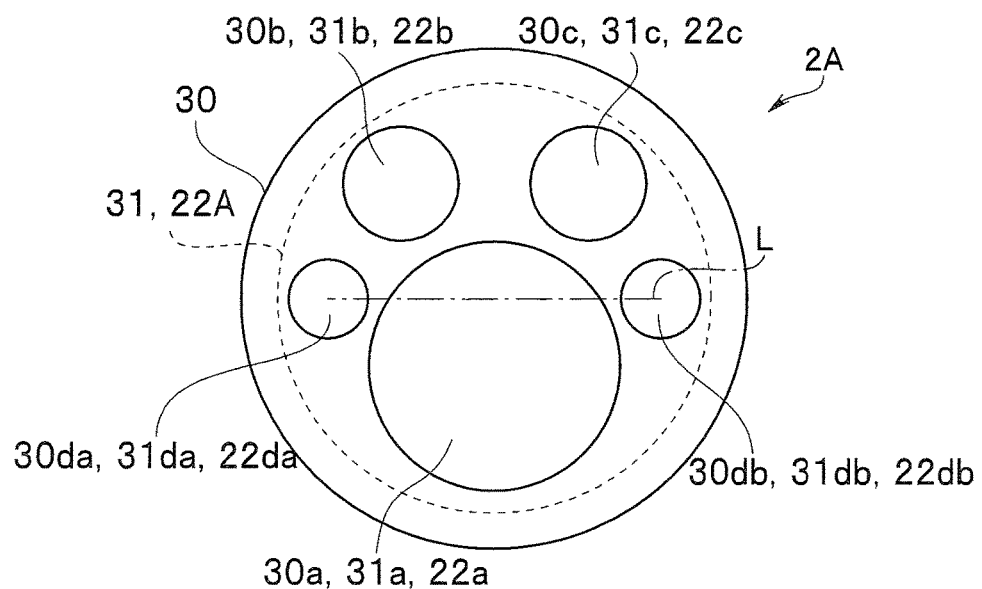
FIG. 8 is a front view of the insertion portion viewed in a direction of an arrow [8] shown in FIG. 7.

FIGS. 7 to 10 are drawings showing the second embodiment of the present invention. In the drawings, FIG. 7 is a side view enlarging and showing the vicinity of a distal end portion of the insertion portion of the endoscope according to the second embodiment of the present invention. FIG. 8 is a front view of the insertion portion viewed in a direction of an arrow [8] shown in FIG. 7. Note that, in FIGS. 7 and 8, a bending operation wire is not shown in order to avoid complication in drawings.

Figure 9:
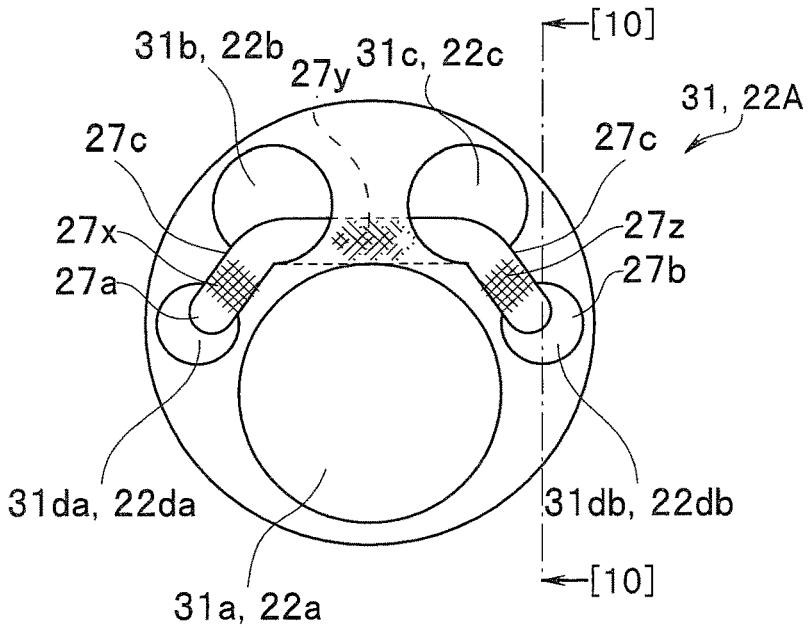
FIG. 9 is a front view showing a configuration in the vicinity of the distal end portion in a state in which a bending operation wire is assembled into the insertion portion of the endoscope according to the second embodiment of the present invention.
Figure 10:
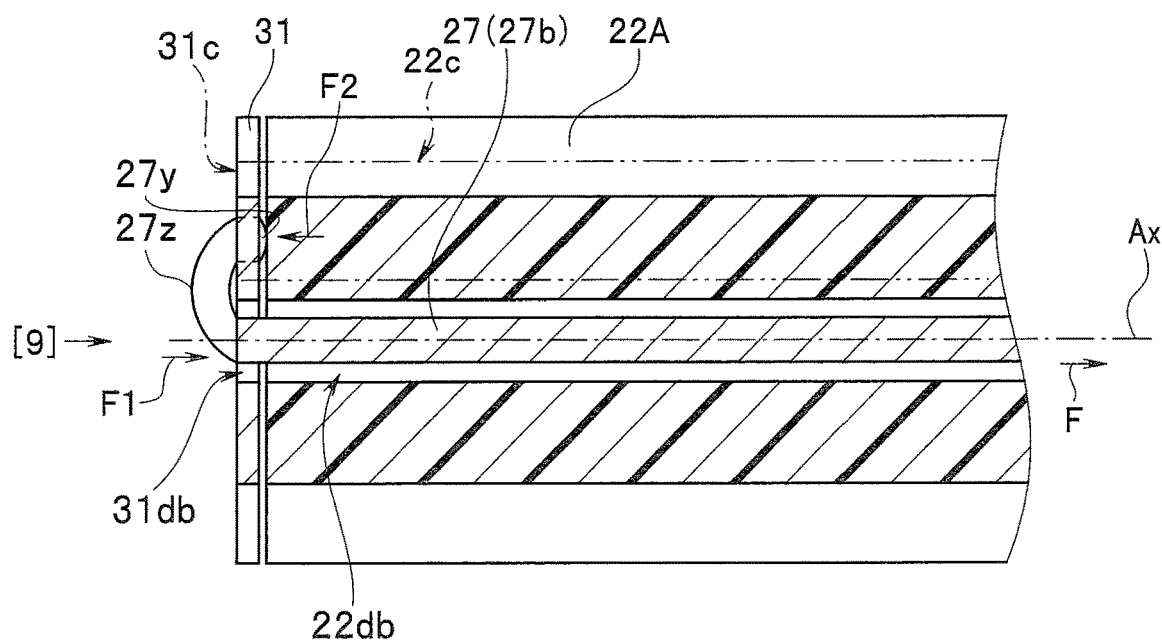
FIG. 10 is a cross-sectional view cut along a line [10]-[10] shown in FIG. 9.

FIG. 9 is a front view showing a configuration in the vicinity of the distal end portion in a state in which the bending operation wire is assembled into the insertion portion of the endoscope according to the second embodiment of the present invention. FIG. 10 is a cross-sectional view cut along a line [10]-[10] shown in FIG. 9. In other words, FIG. 10 is a drawing showing a longitudinal section in a direction along a second wire insertion hole among the plurality of lumens of the multi-lumen tube. Note that, in FIGS. 9 and 10, a distal end rigid member (distal end portion) that is not directly related to the present invention is not shown in order to definitely show the gist (arrangement of the bending operation wire) of the present invention.

According to the first embodiment described above, the cut portion 22v is provided in a part of the multi-lumen tube 22 applied to the insertion portion 2. Thereby, two holes (22b and 22c) in the front face opening are configured so as to form the third wire insertion holes 22ba and 22ca communicating with the proximal end side (the cut portion 22v).

On the other hand, according to the present embodiment, a structure of the multi-lumen tube itself is not retouched and a configuration in which the third wire insertion hole is provided is realized by adding one component with a simple structure (thin plate-like plate member) including a member harder than the multi-lumen tube.

The configuration according to the present embodiment is fundamentally a configuration substantially the same as the configuration of the first embodiment described above. Accordingly, the same components as the components of the first embodiment described above are denoted by the same reference numerals and detailed descriptions are omitted.

In an insertion portion 2A of the endoscope according to the present embodiment, similarly to the first embodiment described above, a distal end portion 6A, a bending portion 7A, and the flexible tube portion 8 are provided and formed in the order from the distal end side (see FIGS. 1 and 7). A structure such that the bending portion 7A is provided at a proximal end of the distal end portion 6A and the flexible tube portion 8 is provided at a proximal end of the bending portion 7A is the same as the structure of the first embodiment described above.

Here, also in the insertion portion 2A of the endoscope according to the present embodiment, a multi-lumen tube 22A is applied to members for configuring the bending portion 7A and the flexible tube portion 8.

Similarly to the first embodiment described above, the multi-lumen tube 22A is a tubular member in which the plurality of lumens (hole; tubular path) communicating with a direction of a long axis (insertion axis) Ax of the insertion portion 2A are formed. As shown in FIG. 8, etc., the multi-lumen tube 22A is the same as the multi-lumen tube 22 of the first embodiment described above in that the multi-lumen tube 22A includes at least the treatment instrument insertion channel 22a, and the first wire insertion hole 22da and the second wire insertion hole 22db provided parallel to the treatment instrument insertion channel 22a.

More specifically, as shown in FIGS. 7 and 8, the multi-lumen tube 22A includes the treatment instrument insertion channel 22a into which a treatment instrument, etc. are inserted, the light wire material insertion hole 22b into which the light guide fiber (LG), etc. are inserted and arranged, the signal line material insertion hole 22c into which an electric signal line such as an image pickup signal cable, the image guide fiber (IG), or the like is inserted and arranged, and the first wire insertion hole 22da, the second wire insertion hole 22db, and the like into which the bending operation wires 27 (not shown in FIGS. 7 and 8, see FIGS. 9 and 10 described later) respectively are inserted.

An arrangement in a surface orthogonal to the long axis Ax of the plurality of lumens (22a, 22b, 22c, 22da, and 22db) is substantially the same as the arrangement of the first embodiment described above.

Note that the second embodiment is the same as the first embodiment in that the first wire insertion hole 22da and the second wire insertion hole 22db are arranged so that the line L (see FIG. 8) connecting the central point of the first wire insertion hole 22da and the central point of the second wire insertion hole 22db passes through at least a part of the treatment instrument insertion channel 22a.

Further, the multi-lumen tube 22A according to the present embodiment differs from the multi-lumen tube 22 according to the first embodiment described above in that the cut portion is not provided.

On the other hand, a plate member 31 is provided on a distal end surface of the multi-lumen tube 22A. The plate member 31 is formed in substantially the same shape as an outer shape of the distal end surface of the multi-lumen tube 22A or in a similar shape and is formed by the thin plate-like plate member. The plate member 31 according to the present embodiment is formed in a substantially circular shape in conformity to the outer shape of the tubular multi-lumen tube 22A.

Further, in conformity to respective front face openings of the plurality of lumens provided on the multi-lumen tube 22A, the same number of the opening holes (31a, 31b, 31c, 31da, and 31db) are drilled in the plate member 31 in substantially the same shape or similar shape and substantially the same size. Any of the plurality of the opening holes (31a, 31b, 31c, 31da, and 31db) are formed penetrating in a thickness direction (a direction of the long axis Ax of the insertion portion 2A) of the plate member 31. Note that, in consideration of working accuracy, tolerance, and the like of the plate member 31, respective sizes of the respective opening holes (31a, 31b, 31c, 31da, and 31db) formed on the plate member 31 side are practically formed such that respective corresponding opening holes become slightly larger than respective sizes of respective front face openings on the multi-lumen tube 22A side.

Further, when the plate member 31 is arranged on the distal end surface of the multi-lumen tube 22A, the plurality of opening holes (31a, 31b, 31c, 31da, and 31db) are arranged in positions in which the plurality of opening holes communicate with the respective front face openings corresponding to the plurality of lumens (22a, 22b, 22c, 22da, and 22db) of the multi-lumen tube 22A.

Note that the plate member 31 is formed by using a hard thin plate-like member using a metal material such as stainless steel or a resin material such as polyether ether ketone (PEEK).

Further, according to the present embodiment, two holes (that is, holes corresponding to the light wire material insertion hole 22b and the signal line material insertion hole 22c respectively; 31b and 31c) of the plurality of opening holes of the plate member 31 are the third wire insertion holes. The two holes (31b and 31c) are formed penetrating in a thickness direction of the plate member 31. The third portion 27c (see FIG. 9) of the bending operation wire 27 described later is inserted and arranged in the third wire insertion holes (31b and 31c) including the two holes.

On the other hand, a distal end rigid portion 30 configuring the distal end portion 6A is provided on the distal end side of the plate member 31. The plurality of opening holes (30a, 30b, 30c, 30da, and 30db) are drilled on the distal end rigid portion 30 so as to correspond to the respective front face openings of the plurality of lumens (22a, 22b, 22c, 22da, and 22db) of the multi-lumen tube 22A and the opening holes (31a, 31b, 31c, 31da, and 31db) of the plate member 31. Note that a detailed configuration of the distal end portion 6A is a part that is not directly related to the present invention and therefore descriptions are omitted. Further, the other configurations are substantially the same as the configurations of the first embodiment described above.

To put it briefly, according to the present embodiment, the multi-lumen tube 22A includes the treatment instrument insertion channel 22a, the first wire insertion hole 22da provided parallel to the treatment instrument insertion channel 22a, and the second wire insertion hole 22db provided parallel to the treatment instrument insertion channel 22a.

Further, according to the present embodiment, as shown in FIG. 9, the bending operation wire 27 that is the one towing wire includes the first portion 27a that is inserted into the first wire insertion hole 22da, the second portion 27b that is inserted into the second wire insertion hole 22db, and the third portion 27c that is provided between the first portion 27a and the second portion 27b and is drawn out between the first wire insertion hole 22da and the second wire insertion hole 22db. Further, in the bending operation wire 27, a proximal end portion (not shown) of the first portion 27a and a proximal end portion (not shown) of the second portion 27b are connected to the bending lever 13 (see FIG. 1) that is a bending operation member (not shown).

Further, according to the present embodiment, the plate member 31 is provided at a position abutting on the distal end surface of the multi-lumen tube 22A. The plate member 31 includes the third wire insertion holes (31b and 31c) including at least two holes that are formed penetrating in a thickness direction.

The third portion 27c of the bending operation wire 27 is inserted into the third wire insertion holes (31b and 31c) and the third portion 27c abuts on a part of the inner side surface (inner peripheral surface) of the plate member 31.

As shown in FIGS. 9 and 10, the bending operation wire 27 is inserted and arranged in the insertion portion 2A of the endoscope according to the present embodiment configured as described above. That the bending operation wire 27 applied to the endoscope according to the present embodiment is the one towing wire is the same as the first embodiment described above.

Here, a procedure when the one bending operation wire 27 is assembled into a predetermined portion of the insertion portion 2A (the multi-lumen tube 22A and the plate member 31) will be described briefly.

Although it is not shown in a drawing, one end portion of the one bending operation wire 27 is first made to be inserted from an opening (not shown; the opening on the proximal end side of the first wire insertion hole 22da of the multi-lumen tube 22A) on the proximal end side (the operation portion 3 side) of the insertion portion 2A. Further, the one end portion of the one bending operation wire 27 is made to be inserted into the distal end side.

Then, as shown in FIG. 9, one end portion of the bending operation wire 27 projects in the forward direction from the opening hole 31da of the plate member 31 corresponding to the front face opening of the first wire insertion hole 22da among the plurality of front face openings of the multi-lumen tube 22A.

Here, a portion that is inserted into the first wire insertion hole 22da is the first portion 27a of the bending operation wire 27.

Subsequently, as shown in FIG. 9, the one end portion of the bending operation wire 27 in a projecting state in the forward direction from the opening hole 31da (the front face opening of the first wire insertion hole 22da) of the plate member 31 is inserted into the opening hole 31b (the third wire insertion hole) of the plate member 31 corresponding to the front face opening of the light wire material insertion hole 22b among the plurality of front face openings of the multi-lumen tube 22A.

In other words, the bending operation wire 27 projects in the forward direction from the opening hole 31*da* (the front face opening of the first wire insertion hole 22*da*) of the plate member 31. Then, the bending operation wire 27 is folded (a cross-hatching portion represented by a reference numeral 27*x* shown in FIG. 9; see the first folded portion) at a front face of the plate member 31 and is inserted into the opening hole 31*b* of the plate member 31.

As described above, while abutting on a rear surface side (a surface facing the distal end surface of the multi-lumen tube 22A) of the plate member 31, the one end portion of the bending operation wire 27 that is inserted from the opening hole 31*b* of the plate member 31 is made to be arranged along the plate member 31 and project in the forward direction from the opening hole 31*c* (the third wire insertion hole) of the plate member 31.

In other words, the bending operation wire 27 is inserted from the opening hole 31*b* of the plate member 31 and then abuts on the rear surface side of the plate member 31 and is here folded (a broken line cross-hatching portion represented by a reference numeral 27*y* shown in FIG. 9; see the second folded portion). Further, the bending operation wire 27 is inserted into the opening hole 31*c* of the same plate member 31 and projects in the forward direction from the opening hole 31*c*.

Subsequently, the one end portion of the bending operation wire 27 in a projecting state in the forward direction from the opening hole 31*c* of the plate member 31 is inserted into the opening hole 31*db* of the plate member 31 corresponding to the front face opening of the second wire insertion hole 22*db* among the plurality of front face openings of the multi-lumen tube 22A. Then, the one end portion of the bending operation wire 27 is directly inserted into the front face opening of the second wire insertion hole 22*db*.

In other words, the bending operation wire 27 projects in the forward direction from the opening hole 31*c* of the plate member 31 and then is folded at the front face of the plate member 31 (a cross-hatching portion represented by a reference numeral 27*z* shown in FIG. 9; see the third folded portion). Further, the bending operation wire 27 is inserted into the front face opening of the second wire insertion hole 22*db* through the opening hole 31*db* of the plate member 31.

As described above, the one end portion of the bending operation wire 27 is made to be inserted into the second wire insertion hole 22*db* and project to the proximal end side from the opening (not shown; the opening on the proximal end side of the second wire insertion hole 22*db* of the multi-lumen tube 22A) of the proximal end side (the operation portion 3 side) of the insertion portion 2A.

Here, a portion that is inserted into the second wire insertion hole 22*db* is the second portion 27*b* of the bending operation wire 27.

Further, the proximal end portion (not shown) of the first portion 27*a* and the proximal end portion (not shown) of the second portion 27*b* in the bending operation wire 27 are finally connected to the bending lever 13 (not shown).

By using such a configuration, when a predetermined bending operation is performed by using the bending lever 13 provided on the operation portion 3, the same action as the action of the first embodiment described above can be obtained.

Note that, according to the configuration of the present embodiment, in a case in which the towing force amount when a towing force is applied to the bending operation wire 27 is large, the distal end surface of the multi-lumen tube 22A can be suppressed from being crushed due to deformation or the like.

In other words, an operation is supposed to be performed in one direction of the bending lever 13 and, for example, as shown in FIG. 10, the second portion 27*b* of the bending operation wire 27 is supposed to be towed in a direction of an arrow F shown in the same FIG. 10. At this time, in the third folded portion 27*z* of the bending operation wire 27, a force amount in a direction of an arrow F1 shown in FIG. 10 is applied to the front face side of the plate member 31. The force amount F1 is dispersed to the whole plate member 31.

On the other hand, in the second folded portion 27*y* of the bending operation wire 27, a force amount in a direction of an arrow F2 shown in FIG. 10 is applied to the rear surface side of the plate member 31. Further, the force amount F2 also is dispersed to the whole plate member 31. Since the force amount F2 is a force amount toward the rear surface side of the plate member 31, a direction of the force amount F2 does not exert an influence on the multi-lumen tube 22A.

Note that, according to the present embodiment also, the bending operation wire 27 is engaged by a frictional force in an abutment portion between the bending operation wire 27 and the plate member 31.

As described above, the force amount applied to a distal end front face of the multi-lumen tube 22A is dispersed or the like, and thereby the plate member 31 suppresses the multi-lumen tube 22A from being crushed.

According to the second embodiment as described above, the plate member 31 is arranged while abutting on the distal end surface of the multi-lumen tube 22A. The plurality of opening holes (30*a*, 30*b*, 30*c*, 30*da*, and 30*db*) that are made to correspond to the plurality of front face openings of the multi-lumen tube 22A are provided and configured in the plate member 31. Further, the two holes (31*b* and 31*c*) among the plurality of opening holes of the plate member 31 are configured as the third wire insertion hole.

By using such a configuration, according to the present embodiment, a structure of the multi-lumen tube 22A itself is not redesigned and one component (the plate member 31) with a simple structure is added. Thereby, the third wire insertion hole (31*b* and 31*c*) is provided to thereby obtain the same effect as the effect of the first embodiment described above.

Further, according to the present embodiment, also in a case in which the towing force amount of the bending operation wire 27 is large, a secure bending operation can be performed while suppressing deformation, etc. of the distal end surface of the multi-lumen tube 22A.

Third Embodiment

Next, an insertion portion of an endoscope according to a third embodiment of the present invention will be described below with reference to FIGS. 11 and 12.

Figure 11:
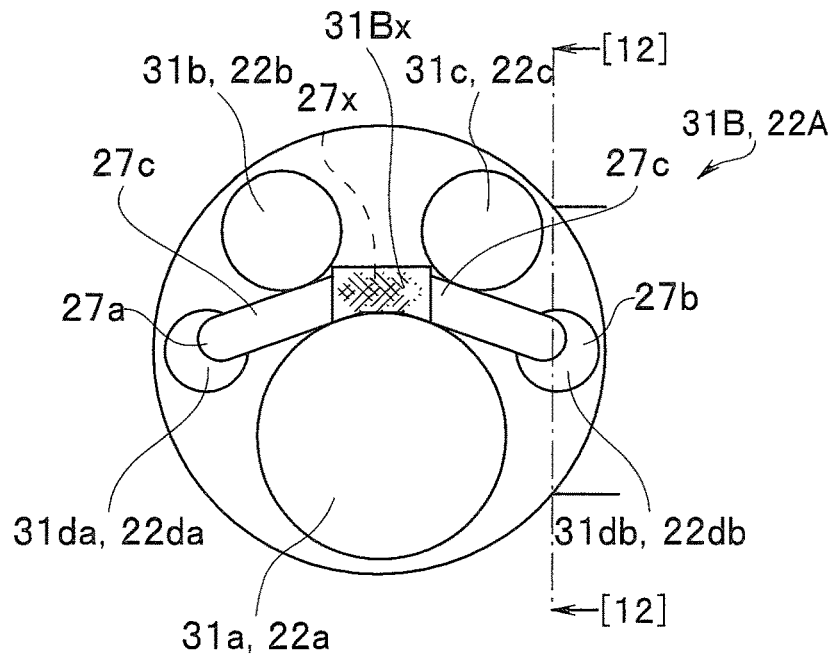
FIG. 11 is a front view enlarging and showing the vicinity of a distal end portion of an insertion portion of an endoscope according to a third embodiment of the present invention.

FIG. 11 is a front view enlarging and showing the vicinity of a distal end portion of the insertion portion of the endoscope according to the third embodiment of the present invention. Note that FIG. 11 is a drawing viewed in a direction of an arrow [11] shown in FIG. 12. FIG. 12 is a cross-sectional view along a line [12]-[12] shown in FIG. 11. Note that, in FIGS. 11 and 12, to avoid complication in drawings, only a multi-lumen tube, a plate member, and a bending operation wire are shown among constituent members of the insertion portion.

A fundamental configuration according to the present embodiment is substantially the same as the configuration of the second embodiment described above. The present embodiment slightly differs from the second embodiment in a configuration of a plate member 31B. Along with the above, the present embodiment slightly differs from the second embodiment in an arrangement of the bending operation wire 27. The other configurations are the same as the configurations of the second embodiment described above. Accordingly, the configurations described in the second embodiment described above are denoted by the same reference numerals and descriptions are omitted. Further, only different portions will be described in detail below.

According to the present embodiment, the plate member 31B includes a projection portion 31Bx that projects in the forward direction. The plate member 31B according to the present embodiment differs from the plate member 31 according to the second embodiment described above in the above-described point.

When the plate member 31B is arranged on the distal end surface of the multi-lumen tube 22A, a penetration hole 31Bw (see FIG. 12) that penetrates in a direction orthogonal to the long axis Ax is formed in the projection portion 31Bx. The penetration hole 31Bw is a third wire insertion hole according to the present embodiment.

Further, the projection portion 31Bx is formed at a position (empty region) such that any of a plurality of opening holes (30a, 30b, 30c, 30da, and 30db) formed on the plate member 31B are not closed. The other configurations are the same as the configurations of the second embodiment described above.

Figure 12:
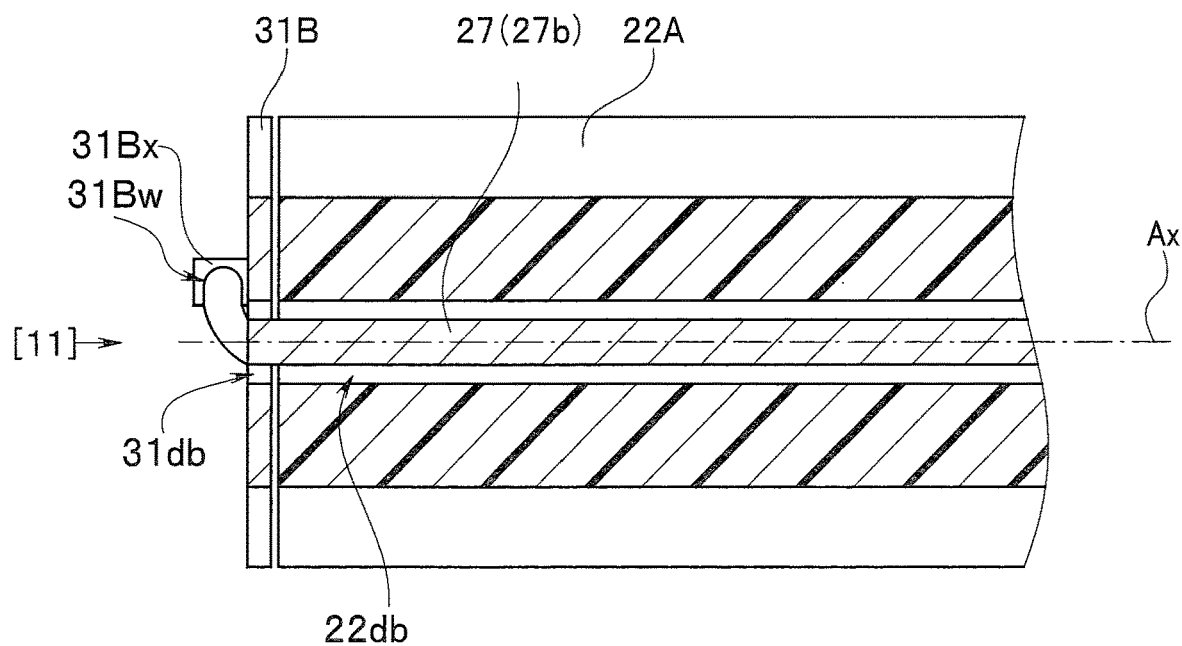
FIG. 12 is a cross-sectional view along a line [12]-[12] shown in FIG. 11.

As shown in FIGS. 11 and 12, the bending operation wire 27 is inserted and arranged in the insertion portion of the endoscope according to the present embodiment configured as described above. The endoscope according to the present embodiment is the same as the endoscope according to each embodiment described above in that the bending operation wire 27 applied to the endoscope according to the present embodiment is the one towing wire.

Here, a procedure when the one bending operation wire 27 is assembled into a predetermined portion of the insertion portion (the multi-lumen tube 22A and the plate member 31B) will be described briefly.

Although it is not shown in a drawing, first, one end portion of the one bending operation wire 27 is inserted from an opening (not shown; the opening on the proximal end side of the first wire insertion hole 22da of the multi-lumen tube 22A) on the proximal end side (the operation portion 3 side) of the insertion portion and the one end portion of the one bending operation wire 27 is made to be inserted into the distal end side.

Then, as shown in FIG. 11, one end portion of the bending operation wire 27 projects in the forward direction from the opening hole 31da of the plate member 31B corresponding to the front face opening of the first wire insertion hole 22da among the plurality of front face openings of the multi-lumen tube 22A.

Here, a portion that is inserted into the first wire insertion hole 22da is the first portion 27a of the bending operation wire 27.

Subsequently, as shown in FIG. 11, the one end portion of the bending operation wire 27 in a projecting state in the forward direction from the opening hole 31da (the front face opening of the first wire insertion hole 22da) of the plate member 31B is made to be inserted into the penetration hole 31Bw (the third wire insertion hole) of the projection portion 31Bx of the plate member 31B. Further, the one end portion of the bending operation wire 27 is made to penetrate in the penetration hole 31Bw of the projection portion 31Bx of the plate member 31B and is made to be inserted into the opening hole 31db (the front face opening of the second wire insertion hole 22db) of the plate member 31B.

In other words, the bending operation wire 27 projects in the forward direction from the opening hole 31da (the front face opening of the first wire insertion hole 22da) of the plate member 31B. Then, the bending operation wire 27 is folded (a cross-hatching portion represented by a reference numeral 27x shown in FIG. 11; see the folded portion) by the projection portion 31Bx at a front face of the plate member 31B and is inserted into the opening hole 31db (the front face opening of the second wire insertion hole 22db) of the plate member 31B. Then, the bending operation wire 27 is directly inserted into the front face opening of the second wire insertion hole 22db. Here, a portion that is inserted into the second wire insertion hole 22db is the second portion 27b of the bending operation wire 27.

Then, the bending operation wire 27 that is inserted into the penetration hole 31Bw (the third wire insertion hole) of the projection portion 31Bx of the plate member 31B is arranged along the penetration hole 31Bw (the third wire insertion hole) while abutting on the penetration hole 31Bw (the third wire insertion hole).

Further, the proximal end portion (not shown) of the first portion 27a and the proximal end portion (not shown) of the second portion 27b in the bending operation wire 27 are finally connected to the bending lever 13 (not shown).

By using such a configuration, when a predetermined bending operation is performed by using the bending lever 13 provided on the operation portion 3, the same action as the action of each embodiment described above can be obtained.

Note that, according to the present embodiment also, the bending operation wire 27 is engaged by a frictional force generated at the abutment portion in the projection portion 31Bx of the plate member 31B.

According to the third embodiment as described above, the projection portion 31Bx is provided on the plate member 31B provided on the distal end surface of the multi-lumen tube 22A. Further, the penetration hole 31Bw formed on the projection portion 31Bx is configured as the third wire insertion hole.

By using such a configuration, according to the present embodiment, a configuration of the plate member 31B is advised. Thereby, it is possible to simplify an arrangement of the bending operation wire 27, and at the same time, it is possible to obtain the same effect as the effect of each embodiment described above.

Note that the present invention is not limited to the above-described embodiment, and it goes without saying that various modifications and applications can be made without departing from the gist of the invention. Further, the embodiments include inventions at various stages, and various inventions can be extracted by appropriately combining a plurality of disclosed components. For example, even if some components are deleted from all the components shown in the one embodiment, if the problem to be solved by the invention can be solved and the effect of the invention can be obtained, a configuration in which this component is deleted can be extracted as an invention. Further, components in different embodiments may be appropriately combined. The invention is not restricted by the specific embodiments thereof except that it is limited by the appended claims.

INDUSTRIAL APPLICABILITY

The present invention can be applied to not only an endoscope control apparatus in a medical field but also to an endoscope control apparatus in an industrial field.

What is claimed is:

1. An insertion portion of an endoscope comprising:
a multi-lumen tube comprising:
   a first lumen having a first wire insertion hole at a distal end face of the multi-lumen tube, and
   a second lumen having a second wire insertion hole at the distal end face of the multi-lumen tube, the first wire insertion hole being offset radially from the second wire insertion hole;
a single towing wire comprising:
   a first wire portion inserted into the first lumen through the first wire insertion hole,
   a second wire portion inserted into the second lumen through the second wire insertion hole, and
   a third wire portion provided between the first wire portion and the second wire portion,
   wherein a first proximal end portion of the first wire portion and a second proximal end portion of the second wire portion are each configured to be connected to a bending operation member; and
one or more third lumens, the third wire portion being inserted into the one or more third lumens such that at least a portion of the third wire portion is anchored at an anchor location on an inner peripheral surface of the one or more third lumens when one or more of the first proximal end portion and the second proximal end portion are pulled proximally.

2. The insertion portion of the endoscope according to claim 1, wherein the one or more third lumens are formed in the distal end face of the multi-lumen tube.

3. The insertion portion of the endoscope according to claim 2, wherein the one or more third lumens comprises two third lumens each having a third wire insertion hole formed at the distal end face of the multi-lumen tube, each of the two third lumens communicating with the inner peripheral surface at the anchor location that is proximal to the distal end face.

4. The insertion portion of the endoscope according to claim 1, further comprising a plate disposed on the distal end face of the multi-lumen tube, the plate having the distal end face, the one or more third lumens penetrating in a thickness direction of the plate, the inner peripheral surface being at the anchor location that is proximal to the distal end face.

5. The insertion portion of the endoscope according to claim 1, wherein the multi-lumen tube comprises a treatment instrument insertion channel having a treatment instrument channel opening located on the distal end face, the treatment instrument channel opening being on a line connecting a center of the first wire insertion hole and a center of the second wire insertion hole.

6. The insertion portion of the endoscope according to claim 5, wherein the first wire insertion hole and the second wire insertion hole are arranged so as to face each other across the treatment instrument insertion channel.

7. The insertion portion of the endoscope according to claim 3, wherein the one or more third lumens are configured to carry one or more of a light guide or a signal line.

8. An endoscope comprising:
the insertion portion of an endoscope according to claim 1.

9. The insertion portion of the endoscope according to claim 1, wherein the one or more third lumens comprises a single third lumen formed at the distal end face such that the single third lumen extends in a radial direction of the multi-lumen tube and the inner peripheral surface is at the anchor location that is distal to the distal end face.

10. An insertion portion of an endoscope comprising:
a multi-lumen tube including a distal end surface,
   a first channel formed in the multi-lumen tube and having a first opening provided at the distal end surface,
   a second channel formed in the multi-lumen tube and having a second opening provided at the distal end surface,
   a third opening provided at the distal end surface; and
   a fourth opening provided at the distal end surface,
a single wire inserted into the first channel, the single wire passing:
   through the first channel and out from the first opening,
   from the first opening and into the third opening,
   from the third opening and out from the fourth opening, and
   from the fourth opening, into the second opening and through the second channel;
wherein the single wire is anchored at an anchor location between the third opening and the fourth opening.

11. The insertion portion of the endoscope according to claim 10, further comprising a third lumen having the third opening on a first end of the third lumen and the fourth opening on a second end of the third lumen, the third lumen being configured to guide the single wire in a radial direction of the multi-lumen tube on the distal end surface.

12. The insertion portion of the endoscope according to claim 10, wherein the third opening and the fourth opening are configured to guide the single wire in a direction away from a connecting line, the connecting line connecting a center of the first opening and a center of the second opening.

13. The insertion portion of the endoscope according to claim 10, wherein the single wire is exposed on the distal end surface between the first opening and the third opening and between the fourth opening and the second opening.

14. The insertion portion of the endoscope according to claim 10, wherein the single wire is provided so as to change from extending in a proximal direction to extending in a distal direction at the anchor location.

15. The insertion portion of the endoscope according to claim 3, wherein the multi-lumen tube comprises a cut out formed on a circumferential surface of the multi-lumen tube such that the two third lumens communicate with each other at the anchor location.

16. The insertion portion of the endoscope according to claim 3, wherein the single towing wire is inserted into only a distal end part of one of the two third lumens and only a distal end part of an other of the two third lumens.

17. The insertion portion of the endoscope according to claim 4, wherein the plate comprises an annular wall configured to attach to the distal end face of the multi-lumen tube.

18. The insertion portion of the endoscope according to claim 10, wherein the multi-lumen tube comprises a treatment channel having a treatment channel opening located on the distal end surface, the third opening and the fourth openings are provided such that the single wire avoids passing over the treatment channel opening.

19. An insertion portion of an endoscope comprising:
a multi-lumen tube comprising:
   a first lumen having a first wire insertion hole at a distal end face of the multi-lumen tube, and
   a second lumen having a second wire insertion hole at the distal end face of the multi-lumen tube, the first wire insertion hole being offset radially from the second wire insertion hole;
a single towing wire comprising:

a first wire portion inserted into the first lumen through the first wire insertion hole, a second wire portion inserted into the second lumen through the second wire insertion hole, and a third wire portion provided between the first wire portion and the second wire portion, the third wire portion having a fold between opposing portions of the third wire portion, wherein a first proximal end portion of the first wire portion and a second proximal end portion of the second wire portion are each configured to be connected to a bending operation member; and an anchor surface for anchoring the fold of the third wire portion relative to the first and second wire portions when one or more of the first proximal end portion and the second proximal end portion are pulled proximally.

20. The insertion portion of the endoscope according to claim 19, wherein the anchor surface is an inner peripheral surface of one or more third lumens.

\* \* \* \* \*